US012569645B2

(12) United States Patent
Tsai et al.

(10) Patent No.: US 12,569,645 B2
(45) Date of Patent: Mar. 10, 2026

(54) CATHETER

(71) Applicant: CONVATEC LIMITED, Flintshire (GB)

(72) Inventors: Mingliang Lawrence Tsai, Holmdel, NJ (US); Pavel Zeliankevich, Chester (GB)

(73) Assignee: CONVATEC LIMITED, Flintshire (GB)

( * ) Notice: Subject to any disclaimer, the term of this patent is extended or adjusted under 35 U.S.C. 154(b) by 492 days.

(21) Appl. No.: 17/717,745

(22) Filed: Apr. 11, 2022

(65) Prior Publication Data

US 2022/0355069 A1     Nov. 10, 2022

Related U.S. Application Data

(63) Continuation of application No. PCT/US2022/024231, filed on Apr. 11, 2022.
(Continued)

(51) Int. Cl.
*A61M 25/00* (2006.01)
*A61M 25/10* (2013.01)

(52) U.S. Cl.
CPC .... *A61M 25/0017* (2013.01); *A61M 25/0068* (2013.01); *A61M 25/1018* (2013.01);
(Continued)

(58) Field of Classification Search
CPC .......... A61M 25/0017; A61M 25/0068; A61M 25/1018; A61M 2202/068; A61M 2210/1067; A61M 25/1002; A61M 25/04
See application file for complete search history.

(56) References Cited

U.S. PATENT DOCUMENTS 3,509,884 A * 5/1970 Bell ................... A61M 25/1011
604/101.05
4,822,338 A * 4/1989 Longmore ........ A61M 25/0074
604/540
(Continued)

FOREIGN PATENT DOCUMENTS

CN          2916746 A1      4/2008
CN          104105524 A     10/2014
(Continued)

OTHER PUBLICATIONS

US 11,433,219 B2, 09/2022, Erbey, II (withdrawn)
(Continued)

*Primary Examiner* — Susan S Su
*Assistant Examiner* — Erin A Kim
(74) *Attorney, Agent, or Firm* — TAFT STETTINIUS HOLLISTER LLP; Ryan O. White; Derek B. Lavender

(57)          ABSTRACT

An example catheter includes a tubular body portion and a cuff. The tubular body portion has a proximal end portion and a distal end portion. The distal end portion defines a distal face of the tubular body portion. The cuff is mounted to the distal end portion and defines a distal face of the cuff. In certain embodiments, the tubular body portion terminates within the cuff such that the distal face of the body portion is positioned proximally of the distal face of the cuff. In certain embodiments, a pocket is formed between the cuff and the body portion. In certain embodiments, the body portion is more rigid than the cuff.

20 Claims, 5 Drawing Sheets

Related U.S. Application Data

(60) Provisional application No. 63/186,528, filed on May 10, 2021, provisional application No. 63/173,814, filed on Apr. 12, 2021.

(52) U.S. Cl.
CPC ................ *A61M 2202/068* (2013.01); *A61M 2210/1067* (2013.01)

(56) References Cited

U.S. PATENT DOCUMENTS

| | | | |
|---|---|---|---|
| 7,727,188 B2 | 6/2010 | Machado et al. | |
| 9,808,606 B2 | 11/2017 | Jin et al. | |
| 11,383,021 B2 | 7/2022 | Henry et al. | |
| 11,400,257 B2 | 8/2022 | Tierney et al. | |
| 11,420,017 B2 | 8/2022 | Hilton et al. | |
| 11,439,819 B2 | 9/2022 | Imran | |
| 11,446,430 B2 | 9/2022 | Hougaard | |
| 11,446,468 B2 | 9/2022 | Havard | |
| 11,484,688 B2 | 11/2022 | Sremcevic | |
| 11,490,983 B2 | 11/2022 | Knapp | |
| 11,497,845 B2 | 11/2022 | Foley | |
| 11,534,325 B2 | 12/2022 | Hvid | |
| 11,690,702 B2 | 7/2023 | Kadron et al. | |
| 11,690,947 B2 | 7/2023 | Gobel | |
| 11,712,327 B2 | 8/2023 | Block | |
| 11,738,171 B2 | 8/2023 | Glithero et al. | |
| 11,766,540 B2 | 9/2023 | Brooks et al. | |
| 11,771,868 B2 | 10/2023 | Palmer | |
| 11,786,696 B1 | 10/2023 | Hughett, Sr. | |
| 11,872,106 B2 | 1/2024 | Ackerman | |
| 11,918,756 B2 | 3/2024 | Hughett, Sr. | |
| 11,937,955 B1 | 3/2024 | Knapp et al. | |
| 11,980,566 B2 | 5/2024 | Sharma et al. | |
| 11,980,721 B2 | 5/2024 | Hilton et al. | |
| 11,980,732 B2 | 5/2024 | Hesse | |
| 2005/0137526 A1* | 6/2005 | Machado .............. | A61M 25/01 604/102.01 |
| 2007/0106320 A1 | 5/2007 | Blix et al. | |
| 2010/0280489 A1* | 11/2010 | Nishtala .............. | A61M 3/0287 604/514 |
| 2012/0101515 A1 | 4/2012 | Barbod | |
| 2014/0052063 A1 | 2/2014 | Gregory et al. | |
| 2014/0336569 A1* | 11/2014 | Gobel ................... | A61F 5/0093 604/101.05 |
| 2014/0358126 A1* | 12/2014 | Gobel ................. | A61M 3/0295 604/328 |
| 2015/0080794 A1 | 3/2015 | Duong et al. | |
| 2015/0231378 A1 | 8/2015 | Pepper | |
| 2017/0325927 A1 | 11/2017 | Gobel | |
| 2018/0229013 A1 | 8/2018 | Tsai | |
| 2018/0311480 A1 | 11/2018 | Gobel | |
| 2019/0275305 A1 | 9/2019 | Gobel | |
| 2020/0046384 A1 | 2/2020 | Llc | |
| 2021/0196292 A1* | 7/2021 | Vale ................... | A61M 25/0045 |
| 2022/0184342 A1 | 6/2022 | Erbey et al. | |
| 2022/0218890 A1 | 7/2022 | Chavan | |
| 2022/0218973 A1 | 7/2022 | Chavan et al. | |
| 2022/0218974 A1 | 7/2022 | Chavan et al. | |
| 2022/0226561 A1 | 7/2022 | Hvid et al. | |
| 2022/0241551 A1 | 8/2022 | Middleton et al. | |
| 2022/0241552 A1 | 8/2022 | Middleton et al. | |
| 2022/0241557 A1 | 8/2022 | Erbey, II et al. | |
| 2022/0249805 A1 | 8/2022 | Pedersen | |
| 2022/0280278 A1 | 9/2022 | Van Der Weegen | |
| 2022/0296355 A1 | 9/2022 | Goebel | |
| 2022/0305232 A1 | 9/2022 | Babu et al. | |
| 2022/0323730 A1 | 10/2022 | Tsai | |
| 2022/0330865 A1 | 10/2022 | Lee et al. | |
| 2022/0347430 A1 | 11/2022 | Pedersen | |
| 2022/0362515 A1 | 11/2022 | Erbey, II et al. | |
| 2022/0362552 A1 | 11/2022 | Imran | |
| 2022/0370180 A1 | 11/2022 | Kadron et al. | |
| 2022/0379001 A1* | 12/2022 | Sharma ................ | A61F 5/4405 |
| 2022/0379075 A1 | 12/2022 | Hilton et al. | |
| 2022/0387751 A1 | 12/2022 | Havard et al. | |
| 2023/0211119 A1 | 7/2023 | Pederson | |
| 2023/0226310 A1 | 7/2023 | Hughett, Sr. | |
| 2023/0277755 A1 | 9/2023 | Hickmott et al. | |
| 2023/0285714 A1 | 9/2023 | Higgy | |
| 2024/0001024 A1 | 1/2024 | Zeuthen et al. | |
| 2024/0001073 A1 | 1/2024 | Brar et al. | |
| 2024/0016997 A1 | 1/2024 | Hickmott et al. | |
| 2024/0050691 A1 | 2/2024 | Bryant | |
| 2024/0050692 A1 | 2/2024 | Novak et al. | |
| 2024/0050693 A1 | 2/2024 | Kandrac et al. | |
| 2024/0050694 A1 | 2/2024 | Kandrac et al. | |
| 2024/0108223 A1 | 4/2024 | Moutinho et al. | |
| 2024/0108857 A1 | 4/2024 | Gohde | |
| 2024/0198041 A1 | 6/2024 | Hughett, Sr. | |

FOREIGN PATENT DOCUMENTS

| | | |
|---|---|---|
| CN | 106999701 A | 8/2017 |
| EP | 2575703 B1 | 7/2015 |
| EP | 3727549 B1 | 6/2022 |
| EP | 4005479 A1 | 6/2022 |
| EP | 4031222 A1 | 7/2022 |
| EP | 4051357 A1 | 9/2022 |
| EP | 4061463 A1 | 9/2022 |
| EP | 4061465 A1 | 9/2022 |
| EP | 4072466 A1 | 10/2022 |
| EP | 4096759 A1 | 12/2022 |
| EP | 4100092 A1 | 12/2022 |
| EP | 3921009 B1 | 8/2023 |
| EP | 3990085 B1 | 8/2023 |
| EP | 3570924 B1 | 9/2023 |
| EP | 4249012 A2 | 9/2023 |
| EP | 3672662 B1 | 10/2023 |
| EP | 3784322 B1 | 11/2023 |
| EP | 3512472 B1 | 2/2024 |
| EP | 4326374 A1 | 2/2024 |
| EP | 4326375 A1 | 2/2024 |
| EP | 4326376 A1 | 2/2024 |
| EP | 4326377 A1 | 2/2024 |
| EP | 4326378 A1 | 2/2024 |
| EP | 4326380 A1 | 2/2024 |
| EP | 3544654 B1 | 3/2024 |
| EP | 3259009 B1 | 4/2024 |
| EP | 4175694 B1 | 5/2024 |
| EP | 3552586 B1 | 6/2024 |
| EP | 4380514 A1 | 6/2024 |
| WO | 2006041496 A1 | 4/2006 |
| WO | 2011139498 A1 | 11/2011 |
| WO | 2016087926 A1 | 6/2016 |
| WO | 2020193619 A2 | 10/2020 |
| WO | 2022108589 A1 | 5/2022 |
| WO | 2022111781 A1 | 6/2022 |

OTHER PUBLICATIONS

CN Office Action; China National Intellectual Property Administration; CN Application No. 202280027927.7; Dec. 12, 2025; 19 pages.
JP Office Action; Japan Patent Office; JP Patent Application No. 2023-562608; Jan. 6, 2026; 4 pages.

* cited by examiner

CATHETER

CROSS-REFERENCE TO RELATED APPLICATIONS

The present disclosure is a continuation of international application number PCT/US22/24231 filed on Apr. 11, 2022 and claims the benefit of U.S. Application No. 63/173,814 filed on Apr. 12, 2021 and U.S. Application No. 63/186,528 filed on May 10, 2021, the disclosures of which are hereby incorporated herein in entirety.

TECHNICAL FIELD

The present disclosure generally relates to catheters and associated systems, and more particularly but not exclusively relates to fecal catheters and associated systems.

BACKGROUND

Indwelling fecal management catheters are often utilized to manage the liquid or semi-liquid fecal matter of non-ambulatory hospital patients. However, many existing fecal management catheters provide a pressure point when the patient is in the sitting position.

U.S. Pat. No. 7,727,188 discloses a balloon catheter in which the balloon is mounted on the end of the catheter in a manner that creates a recess or pocket between the catheter wall and balloon wall. The recess or pocket opens toward the proximal end of the catheter. The rigid end of an introducer element or finger is received in the recess to attach it to the catheter. The distal end of the catheter, with the end of the introducer element in the recess, is inserted and positioned within the bowel by manipulating the introducer element or finger. After the catheter is properly positioned in the bowel, the introducer element or finger is withdrawn, detaching it from the catheter as the end of the introducer element slides out of the recess and then out of the bowel. The balloon is inflated prior to or after the withdrawal of the introducer element to anchor the end of the catheter in position within the bowel. Since the distal end of the catheter is made entirely of soft, compliant material, no soft tissue damage can occur from use of the device, even when the catheter remains in place within the body over an extended time period.

Many existing approaches, including those set forth in the above-referenced document, may suffer from one or more drawbacks or limitations, such as those relating to ease of insertion and/or discouraging soft tissue damage. For these reasons among others, there remains a need for further improvements in this technological field.

SUMMARY

An example catheter includes a tubular body portion and a cuff. The tubular body portion has a proximal end portion and a distal end portion. The distal end portion defines a distal face of the tubular body portion. The cuff is mounted to the distal end portion and defines a distal face of the cuff. In certain embodiments, the tubular body portion terminates within the cuff such that the distal face of the body portion is positioned proximally of the distal face of the cuff. In certain embodiments, a pocket is formed between the cuff and the body portion. In certain embodiments, the body portion is more rigid than the cuff. Further forms, features, and embodiments of the present application will become apparent from review of the drawings and descriptions provided herewith.

DETAILED DESCRIPTION OF ILLUSTRATIVE EMBODIMENTS

Figure 1:
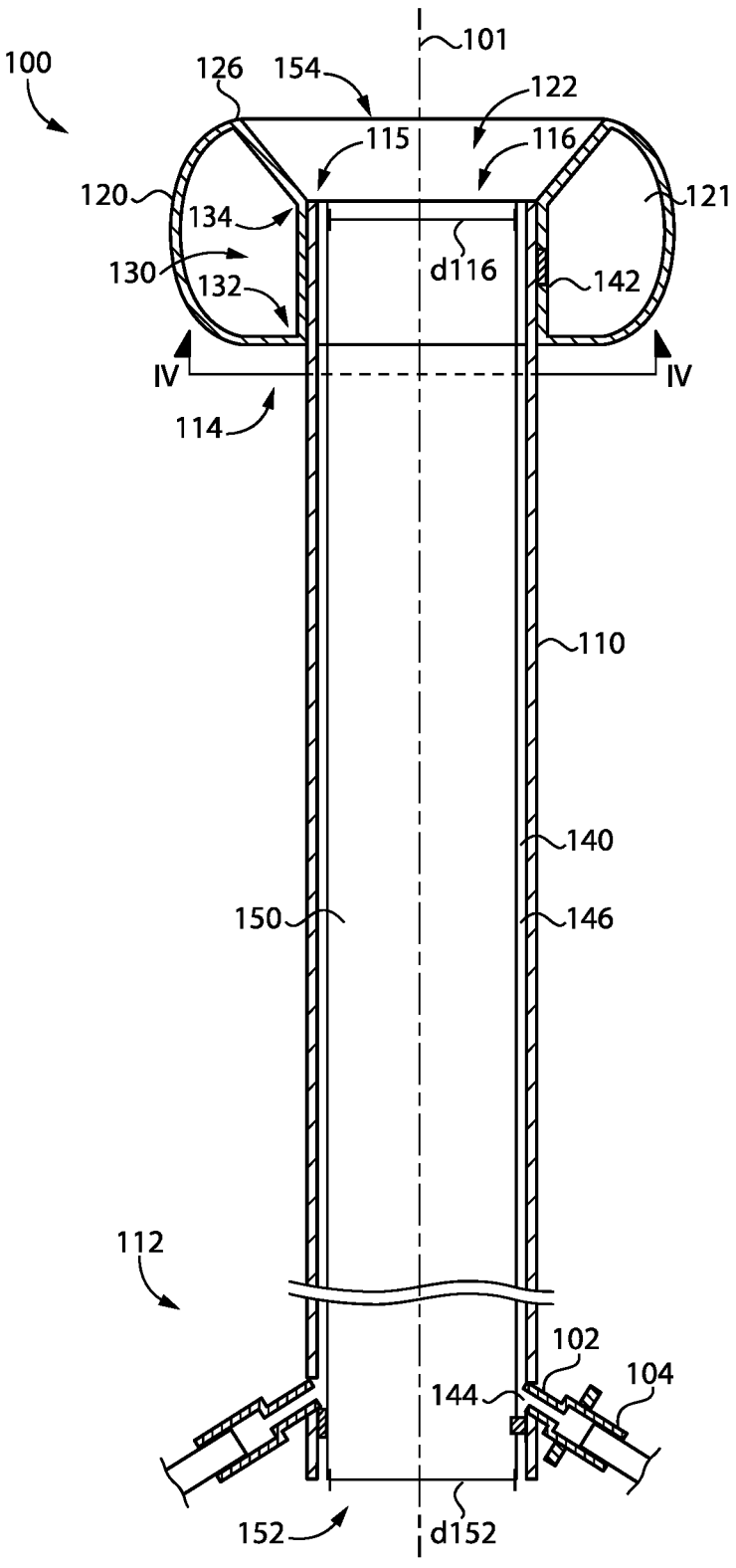
FIG. 1 is a cross-sectional illustration of a catheter according to certain embodiments.

Although the concepts of the present disclosure are susceptible to various modifications and alternative forms, specific embodiments have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described.

Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C). Items listed in the form of "A, B, and/or C" can also mean (A); (B); (C); (A and B); (B and C); (A and C); or (A, B, and C). Further, with respect to the claims, the use of words and phrases such as "a," "an," "at least one," and/or "at least one portion" should not be interpreted so as to be limiting to only one such element unless specifically stated to the contrary, and the use of phrases such as "at least a portion" and/or "a portion" should be interpreted as encompassing both embodiments including only a portion of such element and embodiments including the entirety of such element unless specifically stated to the contrary.

In the drawings, some structural or method features may be shown in certain specific arrangements and/or orderings. However, it should be appreciated that such specific arrangements and/or orderings may not necessarily be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may be omitted or may be combined with other features.

With reference to FIG. 1, illustrated therein is an indwelling catheter 100 according to certain embodiments. The illustrated catheter 100 extends along a longitudinal axis 101 defining a proximal direction (downward in FIG. 1) and an opposite distal direction (upward in FIG. 1), and generally includes a tubular body portion 110 having a proximal end portion 112 and an opposite distal end portion 114, a cuff 120 positioned at the distal end portion 114 of the body portion 110, a finger pocket 130 positioned between the body portion 110 and the cuff 120, an inflation/deflation lumen 140 extending from the cuff 120 to an inflation/deflation port 102, a first fitting 104 mounted to the inflation/deflation port 102, and an evacuation passage 150 defined in part by the body portion 110 and in part by the cuff 120. In the illustrated form, the indwelling catheter 100 is provided in the form of a fecal catheter, and the distal end portion 114 is configured for insertion into a patient's rectum. It is also contemplated that the catheter 100 may be provided in another form, such as that of a urinary catheter or an airway catheter.

The catheter body portion 110 extends from the proximal end portion 112 to the distal end portion 114, and partially defines the inflation/deflation lumen 140 and the evacuation passage 150. The distal end portion 114 includes a tubular wall 117 that is received in a central opening 122 of the cuff 120, and has a distal face 115 defining a body portion inlet 116 having a body portion inlet diameter d116. In the illustrated form, the distal face 115 is positioned within the cuff 120 and proximally of an inlet 154 of the evacuation passage 150. As described herein, the body portion 110 may be provided as a more rigid construction in comparison to the cuff 120, and in certain forms is provided as a non-collapsible tube.

Figure 2:
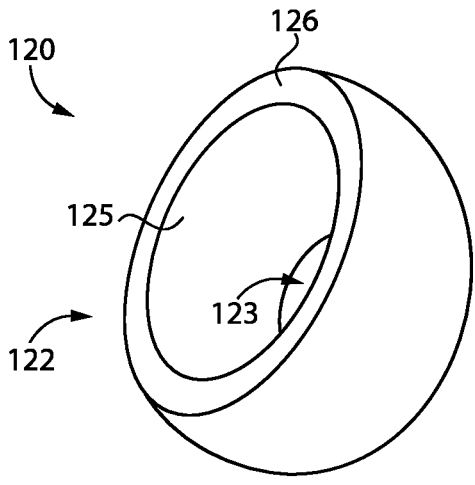
FIG. 2 is a perspective view of a cuff according to certain embodiments.
Figure 3:
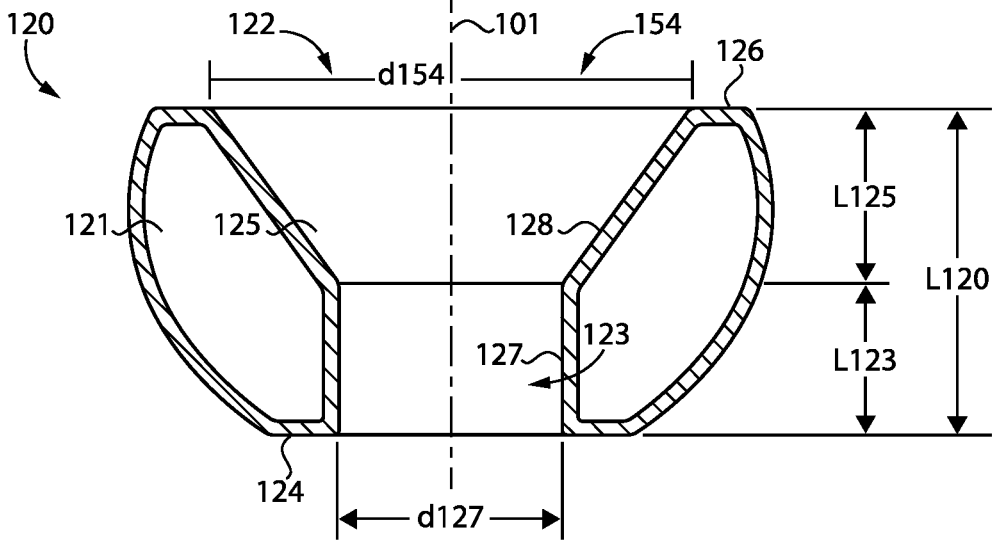
FIG. 3 is a cross-sectional view of the cuff illustrated in FIG. 2.

With additional reference to FIGS. 2 and 3, the cuff 120 is positioned at the distal end of the body portion 110, and defines a chamber 121 and a funnel-shaped central opening 122. The chamber 121 is configured to hold a fluid (e.g., air or saline) when the cuff 120 is in an inflated state, which fluid may be expelled to compress or deflate the cuff 120. As illustrated in FIG. 3, the central opening 122 includes a proximal portion 123 extending from a proximal face 124 of the cuff 120 and a distal portion 125 extending to a distal face 126 of the cuff 120. The proximal portion 123 is sized and shaped to receive the distal end portion 114 of the body portion 110, and is defined by a substantially annular wall 127 having a first inner diameter d127. The distal portion 125 is positioned distally of the proximal portion 123, and is defined by a frustoconical wall 128 that expands from the first diameter d127 to a second diameter d154 greater than the first diameter d127. In the illustrated form, the wall 128 defining the distal portion 125 is substantially frustoconical, and tapers from the second diameter d154 to the first diameter d127 with a constant slope relative to the longitudinal axis 101. It is also contemplated that the distal portion 125 have a convex or concave cross-section.

The cuff 120 has a total longitudinal length L120, which is comprised of a length L123 of the proximal portion 123 and a length L125 of the distal portion 125. In the illustrated form, the proximal portion length L123 is slightly less than half (e.g., about 45%) of the total length L120, and the distal portion length L125 is slightly more than half (e.g., about 55%) of the total length L120. It is also contemplated that other ratios may be utilized. For example, the proximal portion length L123 may be between 40% and 60% of the total length L120. In the illustrated form shown in FIGS. 1 and 3, the distal body portion face 115 is offset from the distal cuff face 126 by the distal portion length L125, which may alternatively be referred to as the offset distance L125.

Figure 4:
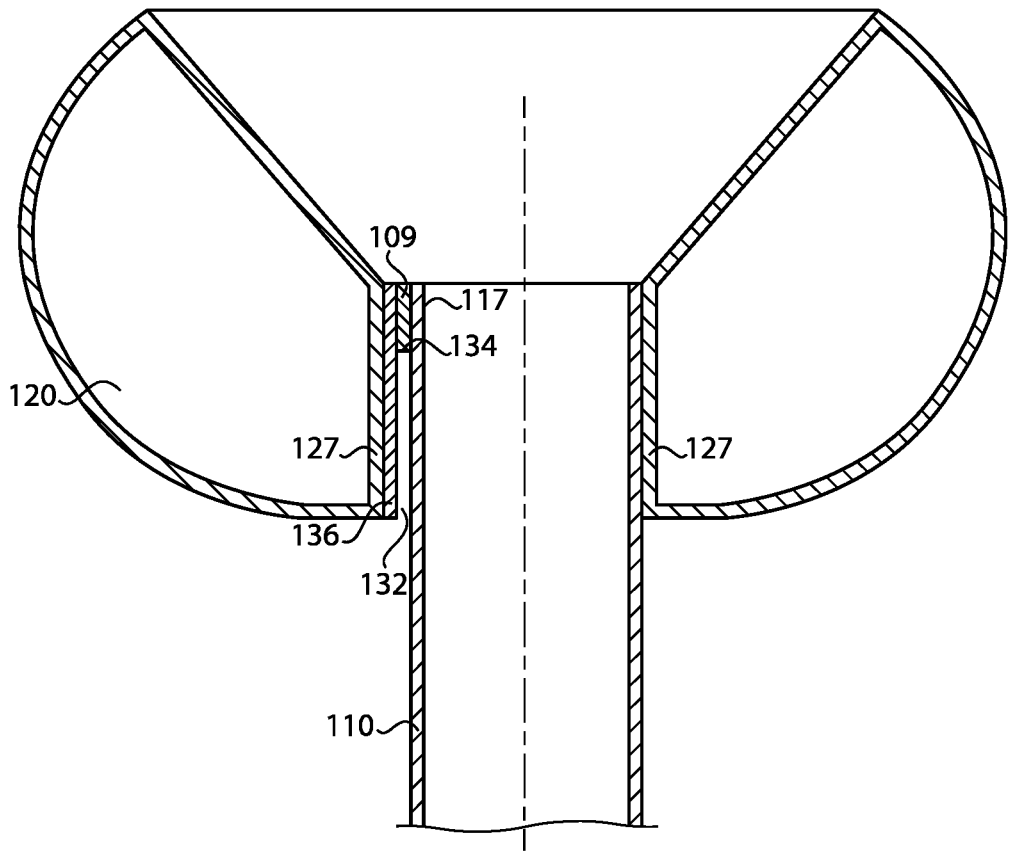
FIG. 4 is a cross-sectional view of a distal end portion of the catheter illustrated in FIG. 1.
Figures 5, 6:
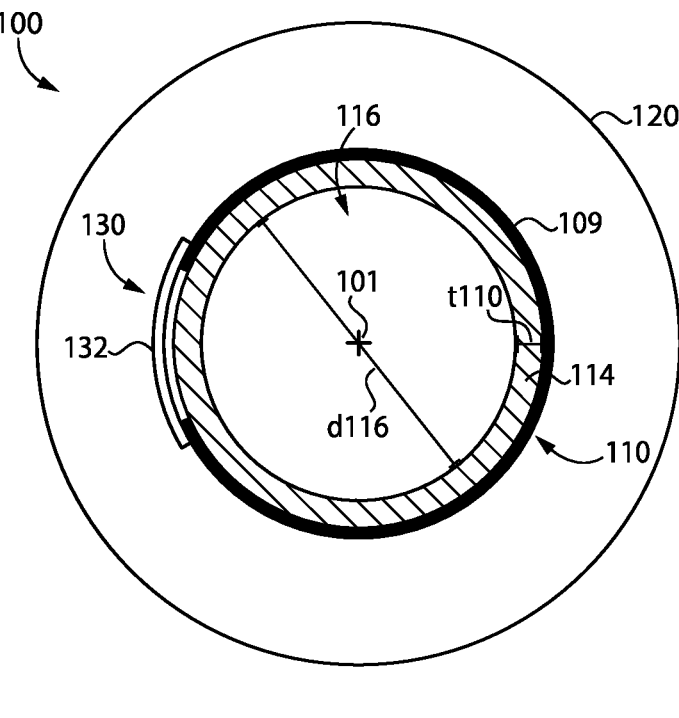
FIG. 5 is a cross-sectional illustration taken along the line IV-IV in FIG. 1.
FIG. 6 illustrates a pocket according to certain embodiments.

With additional reference to FIGS. 4-6, the pocket 130 is positioned in the proximal portion 123 of the opening 122 of the cuff 120, and generally includes an open proximal end 132 and a closed distal end 134. The pocket 130 is positioned between the annular wall 127 and the tubular wall 117 of the distal end portion 114, and may, for example, be adhered to the annular wall 127 and/or the tubular wall 117. The pocket 130 provides an area for receiving a finger or insertion tool to facilitate insertion of the distal portion of the catheter 100 into a patient's orifice (e.g., rectum). In the illustrated form, the pocket 130 is provided as a separate component that is between the annular wall 127 and the distal end portion 114. More particularly, the pocket 130 comprises a first flap 136 that is secured by a sealing 109' on three sides along its periphery 137 to the tubular wall 117 of the body portion 110 such that an inner side of the pocket 130 is defined by the wall 117 and an outer side of the pocket 130 is defined by the flap 136, which is glued to the wall 127. It is also contemplated that the pocket 130 may be defined at least in part by the distal end portion 114. As one example, the open proximal end 132 may be created by omitting a portion of the sealing 109 between the flap 136 and the tubular wall 117 of the body portion 110. Additionally or alternatively, the flap 136 may be secured to the tubular wall 117 of the distal end portion 114 in a manner analogous to that in which the illustrated flap 136 is secured to the annular wall 127.

The inflation/deflation lumen 140 has a distal end 142 that is open to the chamber 121, a proximal end 144 connected with the inflation/deflation port 102, and optionally, a second elongated lumen 146 extending between and connecting the distal end 142 and the proximal end 144 such that the chamber 121 is in fluid communication with the inflation/deflation port 102. As a result, the cuff 120 is operable to be inflated and deflated via the first fitting 104, which may be provided as a normally closed check valve and can be activated into an open passage with a mating syringe.

The evacuation passage 150 is configured to permit fluid (e.g., air, liquid, or semi-liquid) to flow from the inlet 154 to the outlet 152. For example, in the illustrated form, effluent will flow from the inlet 154 to the outlet 152 for discharge from the outlet 152. In certain embodiments, such as those in which the catheter 100 is utilized as an airway catheter, the passage 150 may further facilitate the flow of fluid (e.g., air) from the outlet 152 to the inlet 154, for example during inhalation by the patient.

In the illustrated form, the evacuation passage inlet 154 is defined by the distal face 126 of the cuff 120 and has an inlet diameter d154, and the evacuation passage outlet 152 is defined by the proximal face of the body portion 110 and has an outlet diameter d154 less than the inlet diameter d154. More particularly, the evacuation passage 150 narrows in a distal-to-proximal direction (downward in FIGS. 1 and 4) from the inlet diameter d154 to a third diameter d127 due to the tapered or curved nature of the wall 128, and steps from the third diameter d127 to the outlet diameter d154 due to the thickness t110 of the body portion 110. It is also contemplated that the evacuation passage 150 may narrow in the distal-to-proximal direction in another manner. It has been found that providing the evacuation passage 150 with a larger inlet 154 may aid in enhancing the collection of effluent to be diverted from the patient's cavity.

As noted above, the illustrated catheter body portion 110 is a more rigid construction than the cuff 120, and is optionally provided to not extend all the way to the inlet 154. This offset distance L125 between the distal body portion face 115 and the distal cuff face 126 may reduce the potential pressure point when the patient is in the sitting position.

As also noted above, in the illustrated form, there is a finger pocket 130 in an open envelope, which can be created between the cuff 120 and the catheter body 110 by omitting a portion of the sealing 109 all around the perimeter of the joint between the two components. This finger pocket 130 with an open space recess between the cuff 120 and the catheter body 110 allows a finger or insertion tool to be positioned therein during the insertion of the cuff 120, and may provide the added benefit of not extending a more rigid catheter body 110 all the way to the inlet 154. This feature may likewise minimize the potential pressure point when the patient is in the sitting position. A device without a finger pocket may require a rigid catheter body tip all the way to the distal end in order to facilitate the shuffle of cuff insertion into a body cavity.

Figure 7:
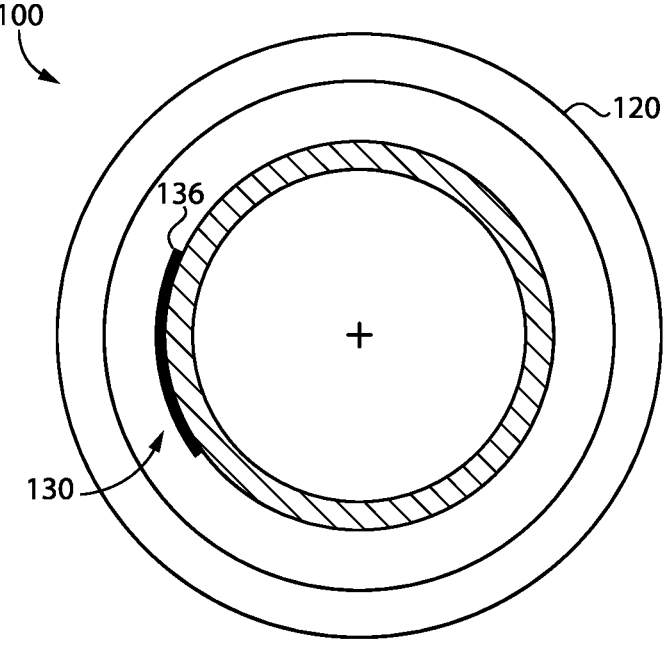
FIG. 7 is another cross-sectional illustration taken along the line IV-IV in FIG. 1.
Figure 8:
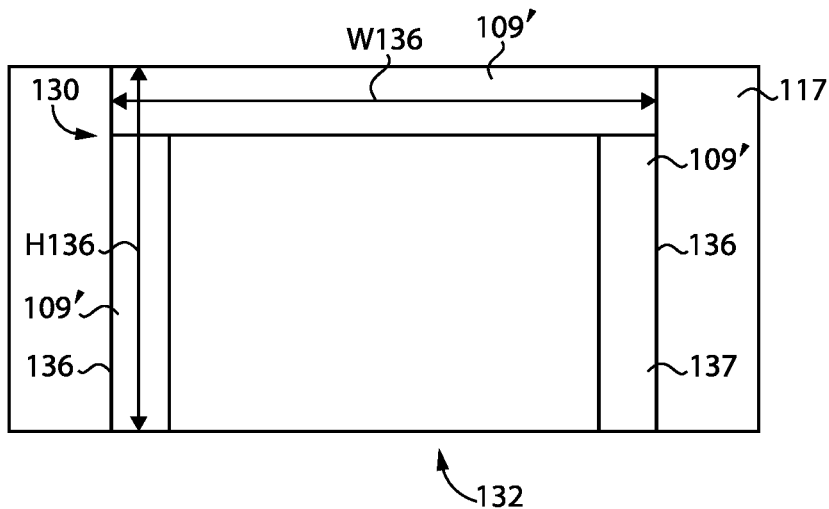
FIG. 8 illustrates a pocket construction according to certain embodiments.

With additional reference to FIGS. 7 and 8, illustrated therein is an alternative arrangement for the pocket 130. The flap 136 has a width W136 and a height H136, and is secured on three sides between the cuff 120 and the distal end portion 114 of the body portion 110 by sealing 109' those three sides. An open proximal end 132 is thus created on the fourth side, which is the only side that is not glued.

Certain embodiments of the present application relate to a catheter 100, comprising: a tubular body portion 110 having a proximal end portion 112 and a distal end portion 114, wherein the distal end portion 114 defines a distal body portion face 115 of the tubular body portion 110; and a cuff 120 mounted to the distal end portion 114 and defining a distal cuff face 126 of the cuff 120; wherein the tubular body portion 110 terminates within the cuff 120 such that the distal body portion face 115 is positioned proximally of the distal cuff face 126.

In certain embodiments, the distal body portion face 115 defines a body portion inlet 116 having a first diameter d116; wherein the distal cuff face 126 defines a cuff inlet 129 having a second diameter d154; and wherein the first diameter d116 is less than the second diameter d154.

In certain embodiments, the tubular body portion 110 has a greater rigidity than the cuff 120.

In certain embodiments, the catheter further comprises a pocket 130 positioned radially between the distal end portion 114 and the cuff 120, wherein the pocket 130 has an open proximal end 132 and a closed distal end 134.

In certain embodiments, the cuff 120 has a longitudinal length L120; wherein an offset distance L125 is defined between the distal body portion face 115 and the distal cuff face 126; and wherein the offset distance L125 is between 40% of the longitudinal length L120 and 60% of the longitudinal length L120.

In certain embodiments, the cuff 120 defines an opening 122 including: a proximal portion 123 having a first diameter d127; and a distal portion 125 that expands in a proximal-to-distal direction from the first diameter d127 to a second diameter d154.

Certain embodiments of the present application relate to a catheter 100 defining an evacuation passage 150, the catheter 100 comprising: a tubular body portion 110 defining a proximal outlet 152 of the evacuation passage 150; and a cuff 120 mounted to a distal end portion 114 of the tubular body portion 110, wherein the cuff 120 defines a distal inlet 154 of the evacuation passage 150; wherein the proximal outlet 152 has a first diameter d152; and wherein the distal inlet 154 has a second diameter d154 greater than the first diameter d152.

In certain embodiments, an opening 122 defined by the cuff 120 narrows in a distal-to-proximal direction from the second diameter d154 to a third diameter d127 corresponding to the first diameter d152.

In certain embodiments, the opening 122 comprises: a distal portion 125 that narrows in the distal-to-proximal direction from the second diameter d154 to the third diameter d127; and a proximal portion 123 that has the third diameter d127.

In certain embodiments, the proximal portion 123 has the third diameter d127 along a longitudinal length L123 thereof; wherein the cuff 120 has a cuff longitudinal length L120; and wherein the longitudinal length L123 of the proximal portion 123 is between 40% of the cuff longitudinal length L120 and 60% of the cuff longitudinal length L120.

In certain embodiments, the tubular body portion 110 has a greater rigidity than the cuff 120.

In certain embodiments, the catheter further comprises a pocket opening 132 defined at an interface between the tubular body portion 110 and the cuff 120.

In certain embodiments, the catheter further comprises a pocket 130 defined radially between the tubular body portion 110 and the cuff 120, the pocket 130 having an open proximal end 132.

Certain embodiments of the present application relate to a catheter 100, comprising: a tubular body portion 110 having a proximal end portion 112 and a distal end portion 114; a cuff 120 defining an opening 122 having a proximal portion 123 and a distal portion 125, wherein the distal end portion 114 of the tubular body portion 110 is received in the proximal portion 123; and a pocket 130 positioned between the tubular body portion 110 and the cuff 120; wherein the tubular body portion 110 has a greater rigidity than the cuff 120.

In certain embodiments, the pocket 130 has an open proximal end 132 and a closed distal end 134.

In certain embodiments, a closed distal end 134 of the pocket 130 is positioned proximally of a proximal face 126 of the cuff 120.

In certain embodiments, a distal body portion face 115 defined by the distal end portion 114 is positioned proximally of a distal cuff face 126 of the cuff 120.

In certain embodiments, an evacuation passage inlet 154 defined by the opening 122 has a first diameter d154; and wherein a diameter of a proximal portion 125 of the opening 122 reduces from the first diameter d154 to a second diameter d127 in a distal-to-proximal direction.

In certain embodiments, the distal end portion 114 has the second diameter d127 as an outer diameter thereof.

In certain embodiments, the tubular body portion 110 is less collapsible than the cuff 120.

Certain embodiments of the present application relate to a cuff 120 for a catheter 100, the cuff 120 comprising: a proximal face 124; a distal face 126 opposite the proximal face 124 and defining an inlet 154 having a first diameter d154; and an opening 122 extending along a longitudinal axis 101 and through the proximal face 124 and the distal face 126, at least a portion of the opening 122 having a second diameter d127 less than the first diameter d154 the opening 122 comprising a first portion 125 open to the inlet 154, wherein the first portion 125 expands from the second diameter d127 to the first diameter d154 in a proximal-to-distal direction.

In certain embodiments, the opening further comprises a second portion 123 positioned proximally of the first portion 125, the second portion 123 having the second diameter d127 along a second portion length L123.

In certain embodiments, the cuff 120 has a cuff longitudinal length L120; and wherein the second portion longitudinal length L123 is between 40% of the cuff longitudinal length L120 and 60% of the cuff longitudinal length L120.

In certain embodiments, the cuff further comprises a pocket 130 positioned within the opening 122, the pocket 130 having an open proximal end 132.

In certain embodiments, the pocket 130 comprises a flap 136; wherein a first portion of a periphery 137 of the flap 136 is secured to a wall 127 that at least partially defines the opening 122; and wherein a second portion of the periphery 137 of the flap 136 is not secured to the wall 127 to thereby define the open proximal end 132.

In certain embodiments, the first portion 125 is frusto-conical.

In certain embodiments, the cuff 120 further comprises a chamber 121 surrounding the opening 122 and operable to receive a fluid for inflation of the cuff 120.

Certain embodiments of the present application relate to a catheter 100 comprising the cuff 120, the catheter 100 further comprising a tubular body portion 110 connected to the cuff 120, wherein a distal body portion face 115 is positioned proximally of the distal face 126 of the cuff 120.

In certain embodiments, a distal end portion 114 of the tubular body portion 110 extends into the opening 122.

In certain embodiments, the tubular body portion 110 is more rigid than the cuff 120.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

8

What is claimed is:

1. A catheter, comprising:
a tubular body portion having a proximal end portion and a distal end portion, wherein the distal end portion defines a distal body portion face of the tubular body portion;
a cuff mounted to the distal end portion and defining a distal cuff face of the cuff, wherein the cuff comprises an opening that is defined at least in part by a wall of the cuff; and
a pocket positioned within the opening and having an open proximal end, wherein the pocket comprises a flap having a periphery, wherein a first portion of the periphery is secured to the wall, and wherein a second portion of the periphery is not secured to the wall to thereby define the open proximal end;
wherein the tubular body portion terminates within the cuff such that the distal body portion face is positioned proximally of the distal cuff face,
wherein an offset distance is defined between the distal body portion face and the distal cuff face; and
wherein the cuff has a longitudinal length, and the offset distance is between 40% of the longitudinal length of the cuff and 60% of the longitudinal length of the cuff.

2. The catheter of claim 1, wherein the distal body portion face defines a body portion inlet having a first diameter;
wherein the distal cuff face defines a cuff inlet having a second diameter; and
wherein the first diameter is less than the second diameter.

3. The catheter of claim 1, wherein the tubular body portion has a greater rigidity than the cuff.

4. The catheter of claim 1, wherein the pocket is positioned radially between the distal end portion and the cuff, and wherein the pocket has a closed distal end.

5. The catheter of claim 1, wherein the opening comprises:
a proximal portion having a first diameter; and
a distal portion that expands in a proximal-to-distal direction from the first diameter to a second diameter.

6. A catheter defining an evacuation passage, the catheter comprising:
a tubular body portion defining a proximal outlet of the evacuation passage; and
a cuff mounted to a distal end portion of the tubular body portion, wherein the cuff defines a distal inlet of the evacuation passage, wherein the tubular body portion extends into an opening that extends through the cuff, and wherein the opening is defined at least in part by a wall of the cuff; and
a flap having a periphery, wherein a first portion of the periphery is secured to the wall, and wherein a second portion of the periphery is not secured to the wall to thereby define an open proximal end of a pocket;
wherein the proximal outlet has a first diameter;
wherein the distal inlet has a second diameter greater than the first diameter, wherein an offset distance is defined between a face of the distal end portion of the tubular body portion and a distal cuff face; and
wherein the cuff has a longitudinal length and the offset distance is between 40% of the longitudinal length of the cuff and 60% of the longitudinal length of the cuff.

7. The catheter of claim 6, wherein an opening defined by the cuff narrows in a distal-to-proximal direction from the second diameter to a third diameter corresponding to the first diameter.

8. The catheter of claim 7, wherein the opening comprises:

a distal portion that narrows in the distal-to-proximal direction from the second diameter to the third diameter; and a proximal portion that has the third diameter.

9. The catheter of claim 8, wherein the proximal portion has the third diameter along a longitudinal length thereof; and wherein the longitudinal length of the proximal portion is between 40% of the cuff longitudinal length and 60% of the cuff longitudinal length.

10. The catheter of claim 6, wherein the tubular body portion has a greater rigidity than the cuff.

11. The catheter of claim 6, further comprising a pocket opening defined at an interface between the tubular body portion and the cuff.

12. The catheter of claim 6, wherein the pocket is defined radially between the tubular body portion and the cuff.

13. A catheter, comprising:

a tubular body portion having a proximal end portion and a distal end portion;

a cuff defining an opening having a proximal portion and a distal portion, wherein the distal end portion of the tubular body portion is received in the proximal portion; and a pocket positioned between the tubular body portion and the cuff, wherein the pocket is defined by a flap having an outer periphery, wherein a first portion of the outer periphery is secured to a wall of the opening, and wherein a second portion of the periphery is not secured to the wall such that the pocket is defined with an open proximal end;

wherein the tubular body portion has a greater rigidity than the cuff, wherein an offset distance is defined between a distal body portion face defined by the distal end portion of the tubular body portion and a distal cuff face; and wherein the cuff has a longitudinal length and the offset distance is between 40% of the longitudinal length of the cuff and 60% of the longitudinal length of the cuff.

14. The catheter of claim 13, wherein the pocket has a closed distal end.

15. The catheter of claim 13, wherein a closed distal end of the pocket is positioned proximally of a proximal face of the cuff.

16. The catheter of claim 13, wherein the distal body portion face defined by the distal end portion is positioned proximally of a distal cuff face of the cuff.

17. The catheter of claim 13, wherein an evacuation passage inlet defined by the opening has a first diameter; and wherein a diameter of a proximal portion of the opening reduces from the first diameter to a second diameter in a distal-to-proximal direction.

18. The catheter of claim 17, wherein the distal end portion has the second diameter as an outer diameter thereof.

19. The catheter of claim 13, wherein the tubular body portion is less collapsible than the cuff.

20. The catheter of claim 2, wherein the cuff comprises a frustoconical annular wall that expands from the first diameter to the second diameter with a constant slope relative to the longitudinal length.

\* \* \* \* \*